United States Patent [19]

Arima et al.

[11] Patent Number: 5,480,438
[45] Date of Patent: Jan. 2, 1996

[54] BIOACTIVE CERAMIC COATED SURGICAL IMPLANT

[75] Inventors: Yuusuke Arima; Shinichi Miyamoto; Kensho Sahira, all of Saitama, Japan

[73] Assignee: Mitsubishi Materials Corporation, Tokyo, Japan

[21] Appl. No.: 125,327

[22] Filed: Sep. 22, 1993

[30] Foreign Application Priority Data

Sep. 22, 1992 [JP] Japan ................................. 4-277888

[51] Int. Cl.$^6$ ................................................ A61F 2/28
[52] U.S. Cl. ........................ 623/16; 606/76; 433/201.1
[58] Field of Search ............................... 623/16; 606/76, 606/77; 433/201.1

[56] References Cited

U.S. PATENT DOCUMENTS

| | | | |
|---|---|---|---|
| 4,159,358 | 6/1979 | Hench et al. | 623/16 |
| 4,330,264 | 5/1982 | Konishi et al. | 432/77 |
| 4,420,304 | 12/1983 | Nakatani et al. | 432/83 |
| 4,655,777 | 4/1987 | Dunn et al. | 623/16 |
| 4,908,030 | 3/1990 | Linkow et al. | 623/16 |
| 5,128,146 | 7/1992 | Hirayama et al. | 623/16 |
| 5,152,791 | 10/1992 | Hakamatsuka et al. | 623/16 |
| 5,164,187 | 11/1992 | Constantz et al. | 623/16 |
| 5,314,475 | 5/1994 | Repenning | 623/16 |

*Primary Examiner*—Paul B. Prebilic
*Attorney, Agent, or Firm*—Vineet Kohli; Thomas R. Morrison

[57] ABSTRACT

A metallic implant base is coated with two bioactive ceramic layers. An inner bioactive ceramic layer is coated on the implant base. An outer bioactive ceramic layer is coated on the inner bioactive ceramic layer. The inner bioactive layer is vitrified at a ratio of not less than 50 volume percent, thereby improving the bonding of the inner bioactive layer to the metallic implant base and preventing migration of the metal ions from the metallic implant base. The outer bioactive ceramic layer is vitrified to a ratio of substantially less than 50 volume percent, thereby providing a desired porosity.

15 Claims, No Drawings

BIOACTIVE CERAMIC COATED SURGICAL IMPLANT

BACKGROUND OF THE INVENTION

The present invention relates to a surgical implant with a metallic base. More specifically, this invention relates to a surgical implant coated with a bioactive ceramic layer which exhibits good adhesion to the metallic implant base.

Prior art surgical implants coated with a bioactive ceramic layer have been used in order to enhance their affinity to bone. Such prior art surgical implants usually have a metallic implant base fabricated from stainless steel, Co—Cr alloy, Ti or a Ti alloy. The metallic implant base is then coated with a ceramic layer consisting essentially of hydroxyapatite or calcium phosphate. Ceramic layers which have added material such as trace amounts of alumina, zirconia or titanic are generally classified as bioactive ceramic materials.

Hydroxyapatite is the most commonly used bioactive ceramic material. Its use is predicated upon its excellent affinity for bone. This property is due to the fact, that hydroxyapatite is a major component of the bones and teeth of living animals.

Hydroxyapatite can be prepared in numerous ways. The most common process for preparing hydroxyapatite is called the wet process. In this process, Hydroxyapatite is produced when a mixture containing $CaHPO_4$ and ammonium hydrogen phosphate is allowed to react. In yet another process, called the dry process, $Ca_3(PO_4)_2$ is allowed to react with CaO in a steam atmosphere at a temperature not lower than 900° C., thereby producing Hydroxyapatite.

Hydroxyapatite can also be prepared by means of a biological process. Japanese laid-open patent publication No. 58-39533 discloses such a process. In a biological extraction process organic matter is extracted from the bones of animals such as an ox or a horse by means of a chemical agent.

Alternatively, the organic matter can be extracted by burning. The powdery hydroxyapatite thus obtained is then welded to the surface of a metallic implant base by spraying or sintering. The resulting metallic implant base has a porous hydroxyapatite layer on its surface.

When used as a surgical implant, this type of implant allows the bone structure to migrate into and proliferate in the pores of the porous hydroxyapatite layer, and anchor itself to the implant. This feature in turn, allows the implant to firmly integrate the underlying bone.

However, use of the aforementioned surgical implant has numerous disadvantages. Chief among them, is the inability of the hydroxyapatite to effectively bind to the metallic implant base. This is due to the porosity of the hydroxyapatite layer. As a result, the surgical implant is not strong and effective in terms of imparting strength to the underling skeletal framework.

Additionally, metal ions from the metallic implant base tend to invade the surrounding bone cells. It is worth noting, that this feature has been linked to bone cancer.

Numerous prior art surgical implants have attempted to overcome the aforementioned deficiencies by providing for an inner and an outer ceramic coated layer.

For instance, Japanese laid-open Patent Publication No. 58-50737 discloses a surgical implant wherein the improvement lies in spraying an inner ceramic layer onto the surface of the metallic implant base. The ceramic layer is made from a ceramic material selected from a group consisting of $Al_2O_3$, $TiO_2$, $ZrO_2$ and $SiO_2$, all of which are non-porous. This inner ceramic layer is supplemented with a porous layer containing hydroxyapatite.

Japanese laid-Open Patent Publication No. 63-160666 also attempts to provide an improved surgical implant. It discloses a surgical implant spray coated with an inner ceramic powder layer, which is further coated with a biologically incompatible metal layer. The inner ceramic powder layer and the biologically incompatible metal layer is supplemented with a outer porous hydroxyapatite layer.

The attempted improvement in the aforementioned surgical implant lies in forming a coat of a biologically incompatible metal layer on a ceramic powder layer, which is then spray coated onto a surface of the metallic base implant. The biological incompatibility of the metal layer is thought to prevent the invasion of the underlying bone cells by the metal ions.

However, the abovementioned surgical implants have numerous disadvantages. Chief among them is the cost of manufacturing the implants. The added cost is attributed to the necessity for coating a powdery ceramic layer with a biologically incompatible metal plating prior to forming an outer porous hydroxyapatite layer on the inner ceramic powder layer.

Additionally, the outer porous hydroxyapatite layer tends to separate when subjected to impact. This is due to its inability to effectively bond to the ceramic powder layer laced with a coat of a biologically incompatible metal.

OBJECTS AND SUMMARY OF THE INVENTION

It is an object of the present invention to provide an improved surgical implant with a metallic implant base.

It is another object of the present invention to provide a surgical implant with improved adhesive properties, the improvement lying in adhering the hydroxyapatite layer to the metal implant base.

It is still another object of the present invention to provide an improved surgical implant which prevents invasion of the underlying bone cells by metal ions, thereby reducing the risk of cancer associated with the migration of metal ions.

Briefly stated, the present invention provides a bioactive ceramic coated surgical implant comprising at least one metallic implant base, an inner layer of a bioactive ceramic which has a vitrification ratio of at least 50 volume percent, and an outer layer of a bioactive ceramic formed on the inner layer, wherein the outer layer has a vitrification ratio (has been vitrified at least by 50 vol %) of less than 50 volume percent.

Briefly stated, the present invention provides a bioactive ceramic coated surgical implant comprising a metallic implant base, which has a surface coating thereon of a bioactive ceramic layer.

According to an embodiment of the invention, there is provided a bioactive ceramic coated surgical implant which comprises a metallic implant base having a surface coating thereon of a bioactive ceramic layer. The bioactive ceramic layer further includes an inner hydroxyapatite layer and an outer porous hydroxyapatite layer. The inner hydroxyapatite layer is vitrified at a ratio of not less than 50 volume percent, and the outer porous hydroxyapatite layer is coated on the inner hydroxyapatite layer. The outer porous hydroxyapatite layer has a porosity substantially greater than the porosity of the inner hydroxyapatite layer.

According to another embodiment of the present invention, there is provided a method of producing a bioactive ceramic coated surgical comprising forming an implant base followed by plasma spraying an inner layer of a bioactive ceramic on the implant base. The method also encompasses controlling conditions of plasma spraying the inner layer to provide a vitrification ratio of at least 50 volume percent. This step is followed by plasma spraying an outer layer of a bioactive ceramic on the inner layer, and controlling conditions of plasma spraying the outer layer to provide a vitrification ratio of substantially less than 50 volume percent, so that the outer layer is substantially more porous than the inner layer.

According to a feature of the present invention, the inner layer includes a hydroxyapatite.

According to another feature of the present invention, both the outer layer and inner layer include hydroxyapatite or a mixture of hydroxyapatite and calcium phosphate.

Additionally, a vitrification ratio of less than 50 volume percent imparts greater porosity to the inner layer, which further weakens the bond between the bioactive inner layer and the metallic implant base.

According to a feature of the present invention, a bioactive ceramic coated surgical implant is provided in which the bioactive ceramic layer includes non-toxic ceramic material selected from the group consisting of glass of $Al_2O_3$, CaO, $TiO_2$, CaO—$Al_2O_3$ and $Al_2O_3$—$SiO_2$.

According to a feature of the present invention, a bioactive ceramic coated surgical implant is provided wherein the bioactive ceramic layer further includes biodegradable glass of $SiO_2$—$Na_2O$—CaO—$P_2O_5$.

DETAILED DESCRIPTION OF THE PREFERRED EMBODIMENT

The term bioactive ceramic as used here generally includes an outer layer and an inner layer of a bioactive ceramic. The ceramic material used to practice this invention should not be toxic to humans. Such a ceramic material may include glass of $Al_2O_3$, CaO, $TiO_2$, CaO—$Al_2O_3$ or $Al_2O_3$—SiO2, or a biodegradable glass of $SiO_2$—$Na_2O$—CaO—$P_2O$. In the present invention it is preferable to use hydroxyapatite as the bioactive ceramic material.

Both the inner and outer layer of the bioactive ceramic may be composed of the following combinations:

(a) Hydroxyapatite;
(b) Calcium phosphate;
(c) a combination of Hydroxyapatite, and a ceramic such as glass of $Al_2O_3$, CaO, $TiO_2$, CaO—$Al_2O_3$ or $Al_2O_3$—SiO2, or a biodegradable glass of $SiO_2$—$Na_2O$—CaO—$P_2O$;
(d) a combination of Calcium phosphate and a ceramic such as glass of $Al_2O_3$, CaO, $TiO_2$, CaO—$Al_2O_3$ or $Al_2O_3$—SiO2, or a biodegradable glass of $SiO_2$—$Na_2O$—CaO—$P_2O$;
(e) Hydroxyapatite and Calcium phosphate;
(f) a combination Hydroxyapatite, Calcium phosphate and a ceramic material such as glass of $Al_2O_3$, CaO, $TiO_2$, CaO—$Al_2O_3$ or $Al_2O_3$—SiO2, or a biodegradable glass of $SiO_2$—$Na_2O$—CaO—$P_2O$.

Two or more of the aforementioned compositions may also be combined.

This invention is illustrated in more detail by reference to the examples described hereinafter.

EXAMPLE 1

A pair of pure Ti bars, measuring 10 cm wide and 10 cm long, were prepared. A plasma jet using a mixture of Ar and He gases was generated, wherein the operating current was 1000 A. The operating voltage was 37 KV. Hydroxyapatite in powder form, having a mean particle size of 10 μm, was fed into the plasma jet at a rate of 0.7 g/min to spray the pure Ti bars. An inner layer of hydroxyapatite was formed on the cross-sectional surfaces and side surfaces of the Ti bars to a thickness of 20 μm. The vitrification ratio of the inner hydroxyapatite layer was 88 volume percent.

The term vitrification ratio of the inner hydroxyapatite layer was 88 volume percent, means that 88 volume percent of the inner layer a was vitrified with the balance being unvitrified.

A plasma jet operating at a 400 A and 33 KV voltage was generated. Hydroxyapatite powder with a mean particle size of 15 μm was supplied to the plasma jet at a rate of 2.5 g/min until an outer layer, 30 μm thick, was formed on the inner hydroxyapatite layer. The outer hydroxyapatite layer had a vitrification ratio of 30 volume percent and was completely porous.

Adhesion Strength Test:

An adhesive was applied to the outer hydroxyapatite layer on the cross-sectional surface of one of the pure Ti bars. The Ti bars were placed together to permit adhesive bonding at their contacting surfaces. After the adhesive had set, the pure Ti bars were pulled apart to measure the adhesion strength between the pure Ti bars and the hydroxyapatite layer in accordance with the invention. The resulting adhesion strength was measured to be 9 kgf/cm$^2$.

Shear Strength Test:

In this test, the outer hydroxyapatite layer on a side surface of the pure Ti bar was adhesive bonded to a side surface of the other pure Ti bar. After the adhesive had set, the pure Ti bars were pulled apart in a direction along the longitudinal axes of the two bars to measure the shear strength. The shear strength was recorded at 3.5 kgf/cm$^2$.

Comparative example 1

In this comparative example, a conventional porous hydroxyapatite layer, 50 μm thick, having a vitrification ratio of 30 volume percent, was formed under the same conditions as those for forming the outer hydroxyapatite layer of the above-described example, using similar pure Ti bars and having the same cross-sectional areas.

Adhesion strength test and shear strength test were conducted using these Ti bars, in accordance with the methods utilized in the above examples. The adhesion strength and the shear strength were respectively recorded as 7 kgf/cm$^2$ and 3 kgf/cm$^2$.

From these results, it is clear that the hydroxyapatite layer formed in accordance with the present invention exhibits superior adhesion strength and shear strength with respect to the metallic implant, when compared to a conventional hydroxyapatite layer.

According to a feature of the present invention, the inner bioactive ceramic layer exhibits superior adhesion strength in relation to the metallic implant base. This is due to the large vitrification ratio of not less than 50 volume percent. At the same time, the inner bioactive ceramic layer exhibits increased bonding strength to the outer porous bioactive ceramic layer. The inner bioactive ceramic layer effectively prevents migration of metal ions. Furthermore, the high porosity of the outer bioactive ceramic layer exhibits affinity for bone.

Having described preferred embodiments of the invention with reference to the accompanying drawing, it is to be understood that the invention is not limited to those precise embodiments, and that various changes and modifications may be effected therein by one skilled in the art without departing from the scope or spirit of the invention as defined in the appended claims.

What is claimed is:

1. A bioactive ceramic coated surgical implant comprising:

at least one metallic implant base;

an inner coating of a bioactive ceramic formed on a surface of said metallic implant base:

said inner coating being vitrified at a ratio of at least 50 vol %;

an outer coating of a bioactive ceramic formed on said inner coating; and said outer coating being vitrified at a ratio of no more than 50 vol %;

said outer coating having a porosity substantially greater than a porosity of said inner coating; and said inner and outer coatings of a bioactive ceramic being composed of at least one material selected from the group consisting of a glass of $Al_2O_3$, CaO, $TiO_2$, CaO—$Al_2O_3$ and $Al_2O_3$—$SiO_2$.

2. The surgical implant of claim 1, wherein said at least said outer coating includes hydroxyapatite.

3. The surgical implant of claim 1, wherein said at least said outer coating includes calcium phosphate.

4. The surgical implant of claim 1, wherein said inner coating and said outer coating include the same bioactive ceramic.

5. The surgical implant of claim 1, wherein said inner coating of a bioactive ceramic and said outer coating of a bioactive ceramic include a mixture of hydroxyapatite and $Ca_3(PO_4)_2$ (calcium phosphate).

6. The surgical implant of claim 1, wherein said inner bioactive ceramic layer and said outer bioactive ceramic layer include a mixture of hydroxyapatite, $Ca_3(PO_4)_2$ (calcium phosphate) and a ceramic; and said ceramic is at least one material selected from the group consisting of a glass of $Al_2O_3$, CaO, $TiO_2$, CaO—$Al_2O_3$, $Al_2O_3$—$SiO_2$ and a biodegradable glass of $SiO_2$—$Na_2O$—CaO—$P_2O_5$.

7. The surgical implant of claim 1, wherein said inner bioactive ceramic coating and said outer bioactive ceramic coating include a mixture of hydroxyapatite and a ceramic; and said ceramic is at least one material selected from the group consisting of a glass of $Al_2O_3$, CaO, $TiO_2$, CaO—$Al_2O_3$ and $Al_2O_3$—$SiO_2$.

8. The surgical implant of claim 1, wherein said inner bioactive ceramic coating and said outer bioactive ceramic coating include a mixture of hydroxyapatite and a ceramic; and said ceramic is at least one material selected from the group consisting of a glass of $Al_2O_3$, CaO, $TiO_2$, CaO—$Al_2O_3$, $Al_2O_3$—$SiO_2$ and a biodegradable glass of $SiO_2$—$Na_2O$—CaO—$P_2O_5$.

9. The surgical implant of claim 1, wherein said inner bioactive ceramic coating and said outer bioactive ceramic coating include a mixture of calcium phosphate and a ceramic; and said ceramic is at least one material selected from the group consisting of a glass of $Al_2O_3$, CaO, $TiO_2$, CaO—$Al_2O_3$ and $Al_2O_3$—$SiO_2$.

10. The surgical implant of claim 1, wherein said inner bioactive ceramic coating and said outer bioactive ceramic coating include a mixture of calcium phosphate and a ceramic; and said ceramic is at least one material selected from the group consisting of a glass of $Al_2O_3$, CaO, $TiO_2$, CaO—$Al_2O_3$, $Al_2O_3$—$SiO_2$ and a biodegradable glass of $SiO_2$—$Na_2O$—CaO—$P_2O_5$.

11. The surgical implant of claim 1, wherein said outer coating of a bioactive ceramic consists essentially of biodegrable glass of $SiO_2$—$Na_2O$—CaO—$P_2O_5$.

12. A bioactive ceramic coated surgical implant comprising:

a metallic implant base;

said metallic implant base having a surface coating thereon of a bioactive ceramic layer;

said bioactive ceramic layer further includes an inner hydroxyapatite layer and an outer porous hydroxyapatite layer;

said inner hydroxyapatite layer is vitrified at a ratio of not less than 50 volume percent;

said outer porous hydroxyapatite layer is coated on said inner hydroxyapatite layer, and said outer porous hydroxyapatite layer having a porosity substantially greater than a porosity of said inner hydroxyapatite layer.

13. The surgical implant of claim 1, wherein said inner coating of a bioactive ceramic consists essentially of biodegradable glass of $SiO_2$—$Na_2O$—CaO—$P_2O_5$.

14. The surgical implant of claim 1, wherein said inner coating of a bioactive ceramic is about 20 µm thick.

15. The surgical implant of claim 12, wherein said inner and outer hydroxyapatite layers have a mean particle size of from 10 to 15 µm.

* * * * *